(12) United States Patent
Dissanayake et al.

(10) Patent No.: US 11,776,161 B2
(45) Date of Patent: Oct. 3, 2023

(54) METHODS FOR IDENTIFYING PORE COLOR

(71) Applicant: The Procter & Gamble Company, Cincinnati, OH (US)

(72) Inventors: Dissanayake Mudiyanselage Mahathma Bandara Dissanayake, Singapore (SG); Akira Matsubara, Singapore (SG); Naoki Miyamoto, Kobe (JP); Ankur Purwar, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 49 days.

(21) Appl. No.: 16/546,837

(22) Filed: Aug. 21, 2019

(65) Prior Publication Data

US 2020/0065998 A1 Feb. 27, 2020

Related U.S. Application Data

(60) Provisional application No. 62/720,143, filed on Aug. 21, 2018.

(51) Int. Cl.
*G06T 7/90* (2017.01)
*G06T 5/40* (2006.01)
(Continued)

(52) U.S. Cl.
CPC ............... *G06T 7/90* (2017.01); *G06T 5/20* (2013.01); *G06T 5/40* (2013.01); *G06T 7/11* (2017.01);
(Continued)

(58) Field of Classification Search
CPC .... G06T 5/20; G06T 5/30; G06T 5/40; G06T 7/11; G06T 7/10; G06T 7/12; G06T 7/90;
(Continued)

(56) References Cited

U.S. PATENT DOCUMENTS 7,415,143 B2 * 8/2008 Grichnik ............... A61B 5/415
382/128
7,531,184 B2 5/2009 Horino et al.
(Continued)

FOREIGN PATENT DOCUMENTS

CN 1961820 A 5/2007
CN 105069818 A 11/2015
(Continued)

OTHER PUBLICATIONS

PCT Search Report and Written Opinion for PCT/US2019/046255 dated Jan. 13, 2020.
(Continued)

*Primary Examiner* — Kenny A Cese
(74) *Attorney, Agent, or Firm* — Alexandra S. Anoff (57) ABSTRACT

A method for identifying a pore color of at least one skin pore. The method includes obtaining at least one image of a subject, extracting a pore image from the obtained image, in which the extracted pore image identifies a boundary of the at least one skin pore, and superimposing the obtained image and the extracted pore image to identify the pore color within the identified boundary of the at least one skin pore.

11 Claims, 8 Drawing Sheets

(51) Int. Cl.
*G06T 5/20* (2006.01)
*G06T 7/11* (2017.01)
*G06T 7/136* (2017.01)

(52) U.S. Cl.
CPC .... *G06T 7/136* (2017.01); *G06T 2207/20212* (2013.01); *G06T 2207/30088* (2013.01); *G06T 2207/30201* (2013.01)

(58) Field of Classification Search
CPC . G06T 2207/20212; G06T 2207/30088; G06T 2207/30201; G06T 2207/30196; G06T 7/136; A61B 5/1032; A61B 5/444
USPC ........ 382/128, 130, 100, 103, 108, 115–118, 382/173, 168, 181, 190
See application file for complete search history.

(56) References Cited

U.S. PATENT DOCUMENTS

| | | | |
|---|---|---|---|
| 7,799,319 B2 | 9/2010 | Takeoka et al. | |
| 8,094,186 B2 | 1/2012 | Fukuoka et al. | |
| 8,591,414 B2 * | 11/2013 | Kitamura | G16H 30/40 |
| | | | 600/306 |
| 8,937,090 B2 | 1/2015 | Kaminuma et al. | |
| 10,812,719 B2 * | 10/2020 | Urakami | G06T 7/246 |
| 2003/0086341 A1 * | 5/2003 | Wells | G10L 15/26 |
| | | | 369/13.56 |
| 2003/0165429 A1 | 9/2003 | Takeoka et al. | |
| 2004/0218810 A1 | 11/2004 | Momma | |
| 2004/0264750 A1 | 12/2004 | Znaiden et al. | |
| 2005/0152930 A1 | 7/2005 | Katsuta et al. | |
| 2006/0034762 A1 | 2/2006 | Takeoka et al. | |
| 2007/0064985 A1 | 3/2007 | Chhibber et al. | |
| 2008/0212894 A1 | 9/2008 | Demirli et al. | |
| 2008/0269304 A1 | 10/2008 | Katsuta et al. | |
| 2009/0028380 A1 | 1/2009 | Hillebrand et al. | |
| 2009/0054744 A1 | 2/2009 | Kitamura et al. | |
| 2010/0084717 A1 | 4/2010 | Tanaka | |
| 2010/0158330 A1 * | 6/2010 | Guissin | A61B 5/445 |
| | | | 382/128 |
| 2010/0309300 A1 * | 12/2010 | Chhibber | G06T 7/0012 |
| | | | 348/77 |
| 2011/0004019 A1 | 1/2011 | Iida et al. | |
| 2012/0008838 A1 * | 1/2012 | Guyon | G06T 7/62 |
| | | | 382/128 |
| 2012/0053243 A1 | 3/2012 | Kaminuma et al. | |
| 2015/0086104 A1 | 3/2015 | Miyamoto et al. | |
| 2015/0213619 A1 * | 7/2015 | Nakamura | G06T 5/002 |
| | | | 382/128 |
| 2017/0206691 A1 | 7/2017 | Harrises et al. | |
| 2017/0270348 A1 | 9/2017 | Morgana et al. | |
| 2017/0270349 A1 | 9/2017 | Polania Cabrera et al. | |
| 2017/0270350 A1 | 9/2017 | Maltz et al. | |
| 2017/0270691 A1 | 9/2017 | Maltz et al. | |
| 2017/0272741 A1 | 9/2017 | Maltz et al. | |
| 2017/0372459 A1 * | 12/2017 | Tan | G06T 5/005 |
| 2019/0096093 A1 * | 3/2019 | Shinoda | G06T 7/11 |
| 2019/0244334 A1 | 8/2019 | Arakawa et al. | |
| 2019/0307231 A1 * | 10/2019 | Katsuyama | G06K 15/22 |
| 2019/0325256 A1 * | 10/2019 | Van Bree | G06K 9/00261 |
| 2020/0034990 A1 * | 1/2020 | Simpson | G06T 7/20 |
| 2020/0065998 A1 | 2/2020 | Dissanayake | |

FOREIGN PATENT DOCUMENTS

| | | |
|---|---|---|
| CN | 107679507 A | 2/2018 |
| FR | 2954837 A | 7/2011 |
| JP | H09175940 A | 7/1997 |
| JP | H09249526 A | 9/1997 |
| JP | H09327333 A | 12/1997 |
| JP | 2000321272 A | 11/2000 |
| JP | 2001190525 A | 7/2001 |
| JP | 2001278739 A | 10/2001 |
| JP | 2002154929 A | 5/2002 |
| JP | 2002265333 A | 9/2002 |
| JP | 2003146840 A | 5/2003 |
| JP | 2004002289 A | 1/2004 |
| JP | 2004364105 A | 12/2004 |
| JP | 2005097218 A | 4/2005 |
| JP | 2005281197 A | 10/2005 |
| JP | 2005345297 A | 12/2005 |
| JP | 2006056852 A | 3/2006 |
| JP | 2006188458 A | 7/2006 |
| JP | 2006305184 A | 11/2006 |
| JP | 2006327972 A | 12/2006 |
| JP | 2007012544 A | 1/2007 |
| JP | 2007055447 A | 3/2007 |
| JP | 2007077066 A | 3/2007 |
| JP | 2007099732 A | 4/2007 |
| JP | 2007204417 A | 8/2007 |
| JP | 2007302583 A | 11/2007 |
| JP | 2007310676 A | 11/2007 |
| JP | 2008019180 A | 1/2008 |
| JP | 2008037764 A | 2/2008 |
| JP | 4286724 B2 | 4/2009 |
| JP | 3150728 U | 5/2009 |
| JP | 2009120545 A | 6/2009 |
| JP | 2009215268 A | 9/2009 |
| JP | 2009242392 A | 10/2009 |
| JP | 2010007525 A | 1/2010 |
| JP | 2010047495 A | 3/2010 |
| JP | 2010047515 A | 3/2010 |
| JP | 2010077072 A | 4/2010 |
| JP | 2010143830 A | 7/2010 |
| JP | 2010260796 A | 11/2010 |
| JP | 2011127954 A | 6/2011 |
| JP | 2011161105 A | 8/2011 |
| JP | 2011184358 A | 9/2011 |
| JP | 2011209243 A | 10/2011 |
| JP | 2012021026 A | 2/2012 |
| JP | 2013196172 A | 9/2013 |
| JP | 2013216602 A | 10/2013 |
| JP | 2014062075 A | 4/2014 |
| JP | 2014120005 A | 6/2014 |
| KR | 100370271 B1 | 1/2003 |
| KR | 100777057 B1 | 11/2007 |
| TW | 201513892 A | 4/2015 |
| WO | 2005070372 A1 | 8/2005 |
| WO | 2007111344 A1 | 10/2007 |
| WO | 2009084156 A1 | 7/2009 |
| WO | 2012014417 A1 | 2/2012 |
| WO | 2012017734 A1 | 2/2012 |
| WO | 2012121309 A1 | 9/2012 |
| WO | 2015045167 A1 | 4/2015 |

OTHER PUBLICATIONS

All Office Actions, U.S. Appl. No. 17/314,115.

Belattar, et al., "Similarity Measures for Content-Based Dermoscopic Image Retrieval: A Comparative Study", In Proceedings of the First International Conference on New Technologies of Information and Communication, Nov. 8, 2015, 6 Pages.

Taeg Sang Cho, et al., "A Reliable Skin Mole Localization Scheme", In Proceedings of the IEEE 11th International Conference on Computer Vision, Oct. 14, 2007, 8 Pages.

Tan, et al., "An Intelligent Decision Support System for Skin Cancer Detection from Dermoscopic Images", In Proceedings of the 12th International Conference on Natural Computation, Fuzzy Systems and Knowledge Discovery, Aug. 13, 2016, pp. 2194-2199.

Unpublished U.S. Appl. No. 17/314,115, filed May 7, 2021, to first inventor Dissanayake Mudiyanselage Mahathma Bandara Dissanayake.

Zhang, et al., "Skin Pores Detection for Image-Based Skin Analysis", In proceedings of the International Conference on Intelligent Data Engineering and Automated Learning, Nov. 2, 2008, pp. 233-240.

Chin Chiun-Li et al: 11 Skin condition 1-16 detection of smart phone face image using multi-feature decision method, Nov. 8, 2017' pp. 379-382.

(56) References Cited

OTHER PUBLICATIONS

Hsiao-hui Li et al. "Based on machine learning for personalized skin care products recommendation engine", International Symposium on Computer, 2020, 3 pgs.

Marc Lievin et al. "Nonlinear Color Space and Spatiotemporal MRF for Hierarchical Segmentation of Face Features in Video" IEEE Transactions on Image Processing, Institute of Electrical and Electronics Engineers, 2004, 13 (1), pp. 63-71. 10.1109/TIP.2003. 818013. hal-00785936.

* cited by examiner

METHODS FOR IDENTIFYING PORE COLOR

FIELD OF THE INVENTION

The present invention relates generally to methods for identifying pore color of a skin pore, especially a facial skin pore, and more particularly, to methods for identifying a skin pore color and determining a skin pore color contrast value, and methods for determining a skin feature color contrast value and/or a skin feature intensity contrast value.

BACKGROUND OF THE INVENTION

Skin features, such as pores, spots and lines, are common concerns in cosmetic dermatology and non-medical cosmetic industries. Presence of enlarged skin pores, for example may negatively impact skin elasticity which would then lead to skin sagging especially around the nose and cheek areas of the face of an individual, which has led many individuals especially younger individuals seeking various treatment options to help address issues related to skin pores. Non-invasive methods are typically used to evaluate skin pores prior to determining a suitable treatment option.

However, some non-invasive methods may not provide the desired level of accuracy for evaluating skin pores. For example, visual grading which involves naked eye examination by an expert or layman can introduce varying degrees of subjectivity, which may result in an inconsistent skin care regimen or skin care product recommendation.

In some instances, a more objective assessment of skin pore may be provided by using a dermascope or confocal laser microscope. However, a limitation of such methods is that only a very small or narrow area (for example, 15 mm in diameter) can be examined at each measurement. As such, it may not be suitable for measuring a larger area such as the entire cheek area or the entire face area as multiple measurements would have to be taken. And in some instances, it may be difficult to provide a desired level of repeatability because it is difficult to relocate the exact same area in each measurement. Another limitation of the above-mentioned methods is that measurements are typically limited to pore number, size, shape and volume.

It has been recently reported that colorimetric features may also be important in the characterization of skin pores, which is important in the assessment of skin pores. However, there are no objective methods established to date to measure skin pore color in vivo. Accordingly, a need exists in the industry for a method for identifying pore color of a skin pore on a subject and color around the skin pore without requiring expensive and specialized equipment such as a dermascope or confocal laser microscope.

SUMMARY OF THE INVENTION

One aspect of the present invention relates to a method for identifying a pore color. The method comprises the steps of obtaining at least one image of a subject, extracting a pore image from the obtained image, wherein the extracted pore image identifies a boundary of the at least one skin pore, and superimposing the obtained image and the extracted pore image to identify the pore color within the identified boundary of the at least one skin pore. The method further comprises the steps of defining an adjacency area radially from the identified boundary of the at least one skin pore, superimposing the obtained image and the defined adjacency area to identify an adjacency area color, and comparing the identified pore color to the identified adjacency area color to determine a pore color contrast value.

Another aspect of the present invention provides for a method for determining a skin feature color contrast value of at least one skin feature, comprising the steps of obtaining at least one image of a subject, extracting a skin feature image from the obtained image, wherein the extracted skin feature image identifies a boundary of the at least one skin feature, defining an adjacency area radially from the identified boundary of the at least one skin feature, superimposing the obtained image and the extracted skin feature image to identify a skin feature color within the identified boundary of the at least one skin feature, superimposing the obtained image and the defined adjacency area to identify an adjacency area color, and comparing the identified skin feature color to the identified adjacency area color to determine the skin feature color contrast value.

Another aspect of the present invention provides for a method for determining a skin feature intensity contrast value of at least one skin feature, comprising the steps of obtaining at least one image of a subject, extracting a skin feature image from the obtained image, wherein the extracted skin feature image identifies a boundary of the at least one skin feature, defining an adjacency area radially from the identified boundary of the at least one skin feature, superimposing the obtained image and the extracted skin feature image to identify an intensity within the identified boundary of the at least one skin feature, superimposing the obtained image and the defined adjacency area to identify an intensity of the adjacency area, and comparing the identified intensity within the identified boundary of the at least one skin feature to the identified intensity of the adjacency area to determine the skin feature intensity contrast value.

Another aspect of the present invention provides for a method for determining an adjacency area color contrast value, comprising the steps of obtaining at least one image of a subject, extracting a skin feature image from the obtained image, wherein the extracted skin feature image identifies a boundary of at least one skin feature, defining an adjacency area radially from the identified boundary of the at least one skin feature, superimposing the obtained image and the defined adjacency area to identify an adjacency area color, obtaining basal skin color, wherein the basal skin color is obtained by identifying skin color of the obtained image, preferably the skin color of the obtained image is identified after the at least one skin feature and the defined adjacency area are removed from the obtained image, and comparing the identified adjacency area color to the obtained basal skin color to determine the adjacency area color contrast value.

These and other aspects of the present invention will become more apparent upon reading the following detailed description of the invention.

Surprisingly and advantageously, the methods for identifying a pore color, as described herein, provide objective means for measuring skin pore color on a subject, and also provide for new pore classifications based on pore color and/or other pore characteristics, such as pore geometry, greatly improving the classification of skin pores, hence improving evaluation methods for determining suitable treatment options, skin care regimen and/or skin care product recommendation. Similarly, the methods for determining a pore color contrast value and/or a pore intensity contrast value also provide for new pore classifications based on one or more of the following: pore color contrast value, pore intensity contrast value, pore color and/or other pore characteristics, such as pore geometry, greatly improving the classification of skin pores.

The methods for identifying a pore color and methods for determining a pore contrast value and/or pore intensity contrast value may be used to identify color, to determine contrast value and/or intensity contrast value of one or more other skin features, which includes, shine, line, spot, hair, mole, pimple, acne, blackhead, whitehead, and combinations thereof.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

The present invention will now be described, by way of illustrative example only, with reference to the accompanying drawings, of which.

DETAILED DESCRIPTION OF THE INVENTION

Features and benefits of the various embodiments of the present invention will become apparent from the following description, which includes examples of specific embodiments intended to give a broad representation of the invention. Various modifications will be apparent to those skilled in the art from this description and from practice of the invention. The scope of the present invention is not intended to be limited to the particular forms disclosed and the invention covers all modifications, equivalents, and alternatives falling within the spirit and scope of the invention as defined by the claims.

As used herein, the term "cosmetic" means a non-medical method of providing a desired visual effect on an area of the human body. The visual cosmetic effect may be temporary, semi-permanent, or permanent.

As used herein, the term "facial area" refers to a user's entire face or a portion of a user's face, including, but not limited to one or more of the following areas: cheek, nose, forehead, mouth, chin, periorbital area and neck area.

As used herein, the term "image capturing device" refers to a device, system or instrument that can capture and/or record images (e.g., still pictures or videos), preferably digital images. The device may be part of a clinical imaging system or a beauty counter skin evaluation system. The device may be part of a mobile device or a smart device, which includes a mobile phone, a smart phone, a tablet, a laptop, a watch, a personal digital assistant, or may be part of a personal computer, or may be a standalone camera such as a handheld camera. The device may also include a built-in light source (e.g., a flash) for emitting light.

As used herein, the term "skin" refers to the outermost protective covering of mammals that is composed of cells such as keratinocytes, fibroblasts and melanocytes. Skin includes an outer epidermal layer and an underlying dermal layer. Skin may also include hair and nails as well as other types of cells commonly associated with skin, such as, for example, myocytes, Merkel cells, Langerhans cells, macrophages, stem cells, sebocytes, nerve cells and adipocytes.

As used herein, the term "skin feature" refers to a feature on the skin of a subject, including, but not limited to one or more of the following: pore, shine, line (including wrinkles), spot, hair, mole, pimple acne, blackhead, whitehead, and any combinations thereof.

As used herein, the term "subject" refers to a person upon whom the use of methods (and systems) described herein.

Disclosed herein are methods for identifying a pore color of at least one skin pore. The method may include obtaining at least one image of a subject, extracting a pore image from the obtained image, wherein the extracted pore image identifies a boundary of the at least one skin pore, and superimposing the obtained image and the extracted pore image to identify the pore color within the identified boundary of the at least one skin pore. The method may further include defining an adjacency area radially from the identified boundary of the at least one skin pore, superimposing the obtained image and the defined adjacency area to identify an adjacency area color, and comparing the identified pore color to the identified adjacency area color to determine a pore color contrast value. Surprisingly, it has been found that the methods for identifying a pore color, as described herein, provide objective means for measuring skin pore color on a subject, and also provide for new pore classifications based on pore color and/or other pore characteristics, such as pore geometry, greatly improving the classification of skin pores, hence improving evaluation methods for determining suitable treatment options, skin care regimen and/or skin care product recommendation. It has also been found that methods for determining a pore color contrast value and/or a pore intensity contrast value also provide for new pore classifications based on one or more of the following: pore color contrast value, pore intensity contrast value, pore color and/or other pore characteristics, such as pore geometry, greatly improving the classification of skin pores. It has also been found that the methods for identifying a pore color and methods for determining a pore contrast value and/or pore intensity contrast value may be used to identify color, to determine contrast value and/or intensity contrast value of one or more other skin features, which includes, shine, line, spot, hair, mole, pimple, acne, blackhead, whitehead, and combinations thereof.

Figure 1:
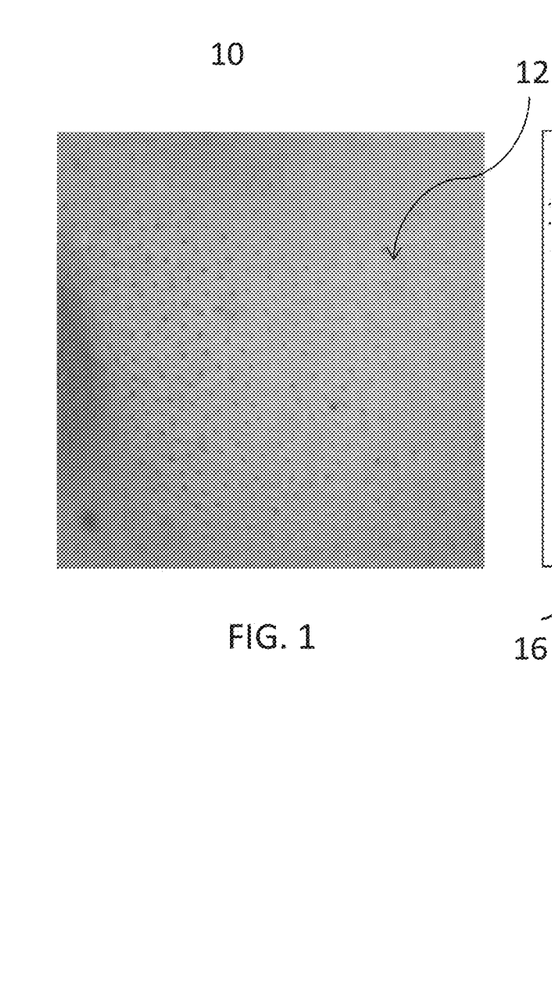
FIG. 1 depicts an image of a cheek area of a subject in accordance with the present invention.

FIG. 1 depicts an image 10 of a cheek area of a subject. The image 10 shows a plurality of skin features 12 such as pores and spots, although a preferably the skin feature is a skin pore, more preferably a facial skin pore. Although the image 10 shows a cheek area in FIG. 1, the image 10 may be of any region of interest such as other facial areas, including, but not limited to, nose, forehead, mouth, chin, periorbital area, and entire face area, and other areas of the human body. The image 10 may be in the form of a color image or a grayscale image.

The image 10 may be obtained from an image capturing device. For example, the image capturing device is an imaging system that uses Canon® 5D Mark II full frame Digital Single Lens Reflex (DSLR) camera with custom light settings and polarization filters, such as Visia®-CR imaging system (Canfield Scientific, New Jersey, USA), which comprises a Canon® 5D Mark II DSLR camera. If the image 10 is an image of an entire face or other large areas of the human body, and the region of interest pertains to only a portion of such an image. A mask may be created so that the image 10 is cropped to show only the region of interest. Optionally, a second (or third or more) image of the subject (e.g., cheek area) may be obtained. The second image may be in the form of a color image or a grayscale image. If two or more images are obtained, preferably at least one of the images is a cross polarized image.

Figure 2:
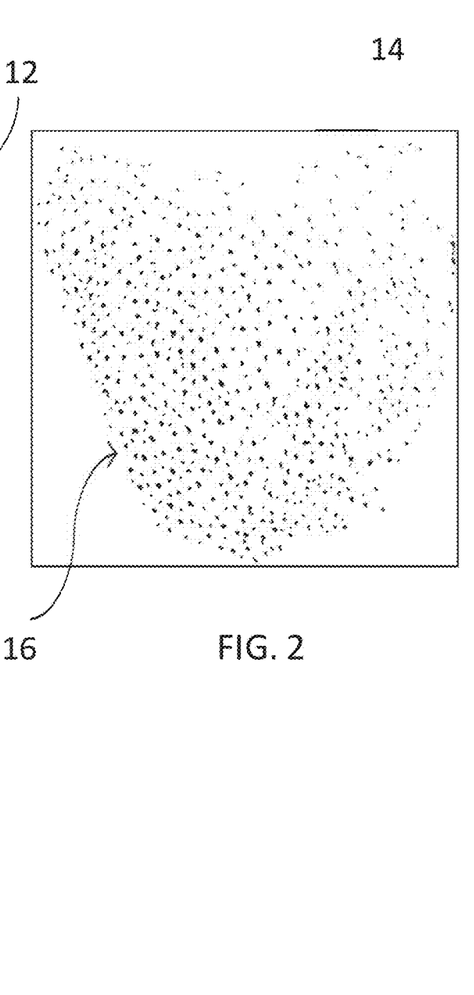
FIG. 2 depicts an extracted pore image from the image of FIG. 1.

After the image 10 is obtained, a pore image 14 comprising a plurality of skin pores 16 is extracted from the image 10 as shown in FIG. 2. It should be appreciated that although the following steps are directed to a pore 16, these steps may be analogized to focus on any one or more skin features beyond a pore. The extracted pore image 14 identifies a boundary of each of the skin pores 16. The pore image 14 may be extracted by segmenting the image 10. Segmentation of the image 10 may be performed by one or more methods, such as a thresholding method, color-based segmentation method, transform method, texture method, or combinations thereof. Preferably, segmentation of image 10 is performed by a thresholding method, and more preferably performed by an adaptive thresholding method.

Optionally, to increase the accuracy of identifying the boundary of each of the skin pores 16, the image 10 may be processed prior to extracting the pore image 14. For example, histogram equalization may be performed to the image 10 for enhancing contrast and/or improving illumination of the image 10 to obtain a histogram-equalized image. The histogram-equalized image or the unprocessed image 10 may be filtered to remove one or more skin features as desired to obtain a filtered image. Filters such as a frequency filter may be used to filter the histogram-equalized image or the unfiltered image 10. Examples of frequency filters include a Fast Fourier Transformation filter used with a Band Pass filter, and a Difference of Gaussian filter. Preferably, a Difference of Gaussian filter is used to filter the histogram-equalized image of the image 10. After the histogram-equalized image or the filtered image is obtained, segmentation is performed on the histogram-equalized image or the filtered image to extract the pore image 14.

Optionally, one or more additional filters may be used to further increase the accuracy of identifying the boundary of each of the skin pores 16. For example, watershed transformation filter may be used to divide skin pores 16 which are connected which otherwise may be identified as a line.

If one or more skin features other than a skin pore, such as shine, line, spot, hair, mole, pimple, acne, blackhead, whitehead, and combinations thereof, is desired, one or more suitable filters may be used to filter the desired one or more skin features for extraction. Such one or more suitable filters includes, but not limited to, a size filter, shape filter, a color filter, an intensity filter. Preferably, the one or more skin features is a facial skin feature.

Figure 3:
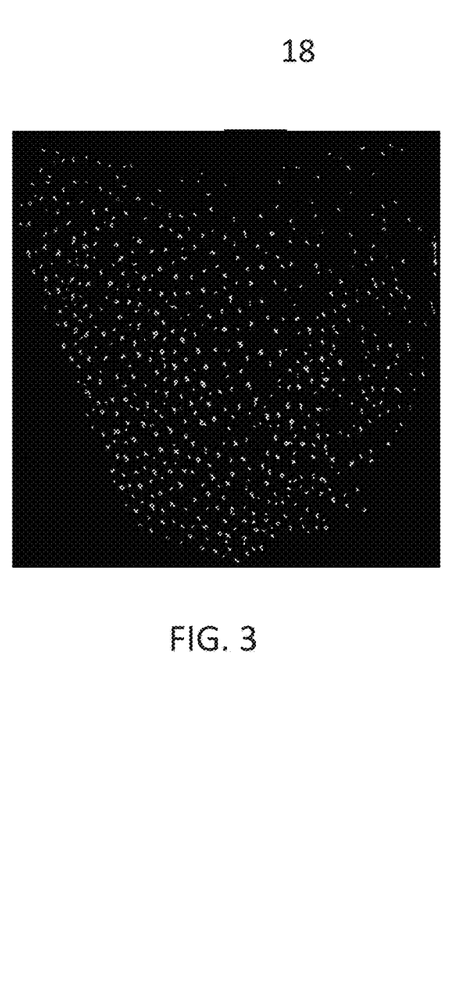
FIG. 3 depicts a superimposed image of the image of FIG. 1 and the extracted pore image of FIG. 2.

The image 10, preferably a color image, is superimposed with the extracted pore image 14 to obtain a superimposed image 18 so as to identify a pore color within the identified boundary of each of the skin pores 16 as shown in FIG. 3. If the image 10 is a color image, the pore color of each of the skin pores 16 may be obtained by identifying the color (i.e. RGB values) or mean color of each of the skin pores 16 and then converting the RGB values into Lab values. Color intensity or color mean intensity of each of the skin pores 16 may also be identified instead of the color. Other methods of calculation may also be used to obtain the pore color, such as XYZ, YCBCR, CMYK, or LCH conversions. If the image 10 is a grayscale image, grayscale intensity or grayscale mean intensity of each of the skin pores 16 may be used instead of RGB values or those value(s) otherwise associated with a color image. Instead of using mean color, color mean intensity, or grayscale mean intensity, other statistical approaches may be used such as the median, standard deviation, entropy, etc.

If one or more skin features other than or in addition to a skin pore is of interest, such feature(s) may be extracted from the image 10 as described above to obtain an extracted one or more skin features image which identifies a boundary of the one or more skin features. The image 10 may be superimposed with the extracted one or more skin features image to obtain a superimposed image so as to identify a skin feature color of each of the one or more skin features within the identified boundary of each of the one or more skin features.

Figure 4:
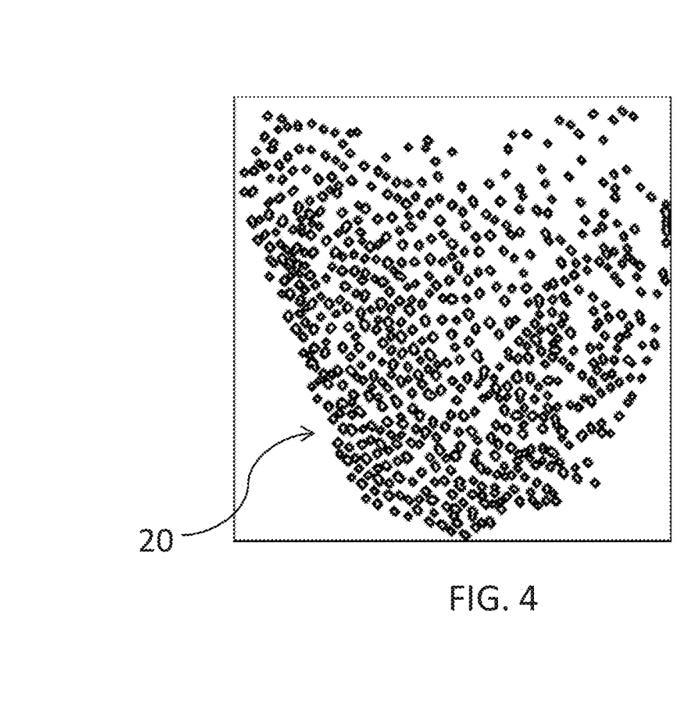
FIG. 4 depicts a defined adjacency area radially from the boundary of each of the pores of FIG. 2.

In addition, an adjacency area 20 that is radial from the identified boundary of each of the skin pores 16 is defined as shown in FIG. 4. Preferably the defined adjacency area 20 of each of the skin pores 16 is in the range of from 0.001 mm to 30 mm, preferably from 0.001 mm to 3.5 mm, and more preferably from 0.005 mm to 1 mm, from the identified boundary of each of the skin pores 16.

The spatial resolution of the Visia®-CR imaging system is about 29 pixels per mm Therefore, when the Visia®-CR imaging system is used to capture the image 10, the defined adjacency area 20 of each of the skin pores 16 is in the range of from 0.029 pixels to 870 pixels, preferably from 0.029 pixels to 101.5 pixels, and more preferably from 0.145 pixels to 29 pixels.

Figure 5:
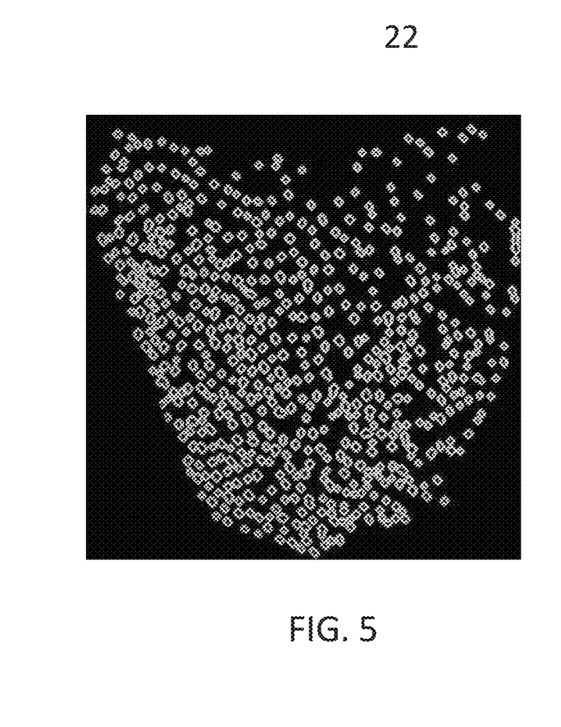
FIG. 5 depicts a superimposed image of the image of FIG. 1 and the defined adjacency area image of FIG. 4.

The image 10 is then superimposed with the defined adjacency area 20 of each of the skin pores 16 to obtain a superimposed image 22 so as to identify an adjacency area color as shown in FIG. 5. If the image 10 is a color image, the adjacency area color of each of the skin pores 16 may be obtained by identifying the color (i.e. RGB values) or mean color of each of the defined adjacency area 20 and then converting the RGB values into Lab values. Color intensity or color mean intensity of each of the defined adjacency area 20 may also be identified instead of the color. Other methods of calculation may also be used to obtain the adjacency area color, such as XYZ, YCBCR, CMYK, or LCH conversions. If the image 10 is a grayscale image, grayscale intensity or grayscale mean intensity of each of the adjacency area may be used instead of RGB values. Instead of using mean color, color mean intensity, or grayscale mean intensity, other statistical approaches may be used such as the median, standard deviation, entropy, etc. Intensity refers to the average value of one or more pixels in a particular space of interest (e.g., the skin pore 16, the adjacency area 20, basal skin, any skin feature of interest).

The identified pore color of each of the skin pores 16 may be compared with the identified adjacency area color of the respective skin pore 16 to determine a pore color contrast value for each of the skin pores 16.

If one or more skin features other than or in addition to a skin pore is of interest, such feature(s) may be extracted from the image 10 as described above to obtain an extracted one or more skin features image which identifies a boundary of the one or more skin features. Preferably, an adjacency area that is radial from the identified boundary of the one or more skin features may be defined. The image 10 is then superimposed with the defined adjacency area of each of the one or more skin features to obtain a superimposed image so as to identify an adjacency area color. The identified skin feature color of each of the one or more skin features may be compared with the identified adjacency area color of the respective skin feature to determine a skin feature color contrast value for each of the one or more skin features.

Advantageously, skin pores may be classified into a predetermined class based on one or more of the following: pore color, pore contrast value, pore intensity contrast value, pore geometry, age of pore, and any combinations thereof. Pore geometry includes, but not limited to, one or more of the following: shape, size, area, volume, aspect ratio, circumference and orientation of a skin pore. For example, the predetermined class may be based on pore size and each pore may be classified into one of the following classifications: invisible pores, visible pores, enlarged pores. The predetermined class may be based on pore color and each pore may be classified into one of the following classifications: dark pores, light pores. The predetermined class may be based on age of pore and each pore may be classified into one of the following classifications: young pore, aged pore.

Advantageously, one or more skin features may be classified into a predetermined class based on one or more of the following: skin feature color, skin feature contrast value, skin feature intensity contrast value, skin feature geometry, age of skin feature, and any combinations thereof. Skin feature geometry includes, but not limited to, one or more of the following: shape, size, area, volume, aspect ratios, circumference and orientation of a skin feature.

Figure 6:
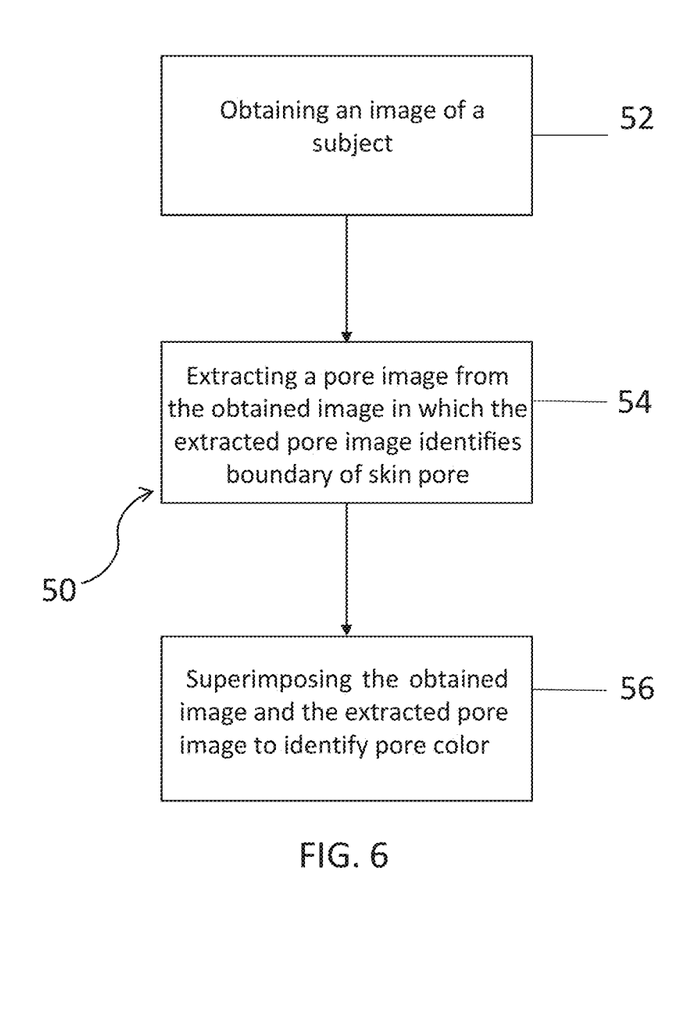
FIG. 6 depicts a flowchart for identifying a pore color in accordance with the present invention.

There is described hereinafter a method 50 for identifying the pore color (or skin feature color) of each of the skin pores 16 in accordance with the present invention. As depicted in FIG. 6, the method 50 comprises obtaining the image 10 of the subject in a step 52, extracting the pore image 14 from the image 10 in which the extracted pore image 14 identifies the boundary of each of the skin pores 16 in a step 54, and superimposing the image 10 and the extracted pore image 14 to identify the pore color within the identified boundary of each of the skin pores 16 in a step 56.

Figure 7:
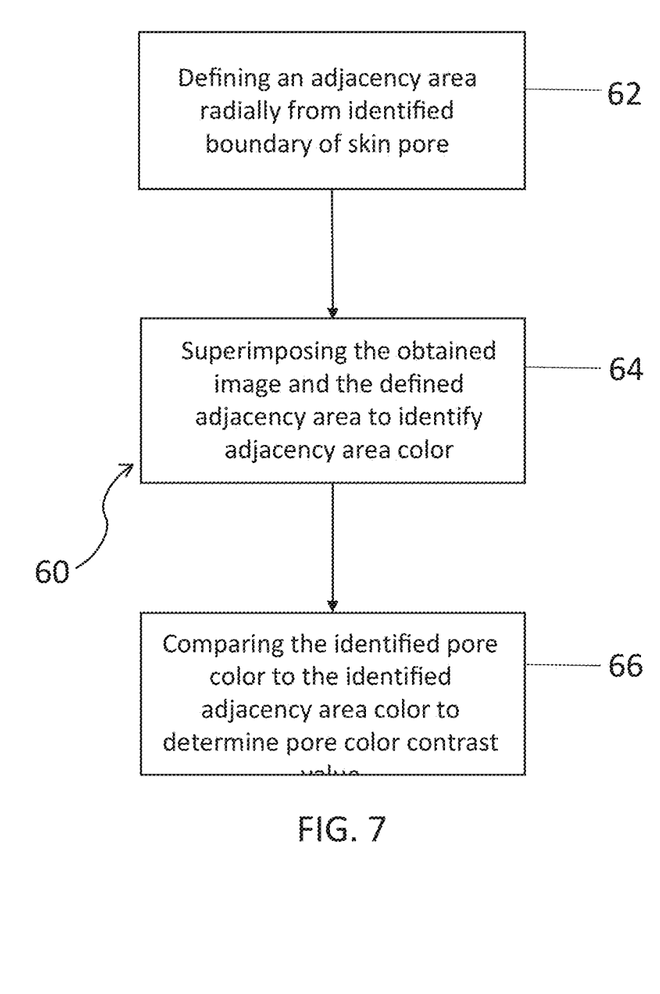
FIG. 7 depicts a flowchart for determining a pore color contrast value based on the pore color of FIG. 6 in accordance with the present invention.

There is described hereinafter a method 60 for determining the pore color contrast value (or skin feature color contrast value or skin feature intensity contrast value) of each of the skin pores 16 in accordance with the present invention. The method 60 comprises defining the adjacency area 20 radially from the identified boundary of each of the skin pores 16 in a step 62, superimposing the image 10 and the defined adjacency area 20 to identify an adjacency area color in a step 64, and comparing the identified pore color obtained in the method 50 to the identified adjacency area color to determine the pore color contrast value of each of the skin pores 16 in a step 66, as shown in FIG. 7. The defined adjacency area is in the range of from 0.001 mm to 30 mm, preferably from 0.001 mm to 3.5 mm, and more preferably from 0.005 mm to 1 mm, from the identified boundary of each of the skin pores 16.

Optionally, to increase the accuracy of identifying the boundary of each of the skin pores 16, the image 10 may be processed prior to extracting the pore image 14. In the step 52 of obtaining the image 10, the step 52 may further include image processing steps such as performing histogram equalization to the image 10 to obtain the histogram-equalized image. The step 52 may also further include a step of filtering the histogram-equalized image or filtering the image 10 for removing one or more skin features that is not a skin pore to obtain the filtered image. The one or more skin features may be selected from the group consisting of shine, line, spot, hair, mole, pimple, acne, blackhead, and whitehead, and combinations thereof. Preferably, the one or more skin feature is a facial skin feature. The step of filtering comprises using a frequency filter such as a Fast Fourier Transformation filter followed by a Band Pass filter, or a Difference of Gaussian filter. Preferably, a Difference of Gaussian filter is used.

In the step 54 of extracting the pore image 14, the pore image 14 is extracted by segmenting one or more of the following: the image 10, the histogram-equalized image and the filtered image. The step of segmenting is performed by one or more of the following methods: thresholding method, color-based segmentation, transform method, texture method, or combinations thereof. Preferably, the segmenting is performed by a thresholding method, and more preferably the segmenting is performed by an adaptive thresholding method.

The method 50 and/or the method 60 further comprises a step of classifying the skin pores 16 into a predetermined class based on one or more of the following: pore color, pore contrast value, pore intensity contrast value, pore geometry, age of pore, and any combinations thereof. Pore geometry includes, but not limited to, one or more of the following: shape, size, area, volume, aspect ratio, circumference, and orientation of a skin pore. For example, the predetermined class may be based on pore size, and each pore may be classified into one of the following classifications: invisible pores, visible pores, enlarged pores. The predetermined class may be based on pore shape, and each pore may be classified into one of the following classifications: round pores, elongated pores. The predetermined class may be based on pore color, and each pore may be classified into one of the following classifications: dark pores, light pores. The predetermined class may be based on age of pore, and each pore may be classified into one of the following classifications:

young pore, aged pore. The predetermined class may be based on a combination of pore color and pore size, and each pore may be classified into one of the following classifications: pores that are dark and elongated, pores that are light and round, pores that are dark and round, pores that are light and elongated.

There is described hereinafter a method for determining an adjacency area color contrast value in accordance with the present invention. The method comprises a first step of obtaining an image of a subject. The image may be obtained from an image capturing device, like the image 10 as described above. The image may be of any region of interest such as other facial areas, including, but not limited to, nose, forehead, mouth, chin, periorbital area, and entire face area, and other areas of the human body, and may be in the form of a color image or a grayscale image. A mask may be created so that the image is cropped to show only a region of interest.

The method comprises a second step of extracting a skin feature image from the obtained image, in which the extracted skin feature image identifies a boundary of at least one skin feature.

The method comprises a third step of defining an adjacency area is radially from the identified boundary of the at least one skin feature. The defined adjacency area is in the range of from 0.001 mm to 30 mm, preferably from 0.001 mm to 3.5 mm, and more preferably from 0.005 mm to 1 mm, from the identified boundary of the at least one skin feature.

The method comprises a fourth step of superimposing the obtained image and the defined adjacency area to identify an adjacency area color. The adjacency area color may be identified based on the method of identifying the color of the defined adjacency area 20 as described above.

The method comprises a fifth step of obtaining basal skin color by identifying skin color of the obtained image. Preferably, the obtained image shows only a region of interest or is cropped to show only a region of interest. Preferably, the skin color of the obtained image is identified after the at least one skin feature and the defined adjacency area are removed from the obtained image. The basal skin color may be identified based on the method of identifying the color of the defined adjacency area 20 or the method of identifying the color of the skin pore 16, as described above.

The method comprises a sixth step of determining the adjacency area color contrast value by comparing the identified adjacency area color to the obtained basal skin color.

The adjacency area color and the basal skin color may be identified by performing the method 50 for identifying the pore color or skin feature color as described above. The adjacency area color contrast value may be determined by performing the method 60 for determining the pore color contrast value (or skin feature color contrast value or skin feature intensity contrast value) as described above.

EXAMPLE

Pore Color and Pore Color Contrast Value of Facial Skin Pores

Figure 8:
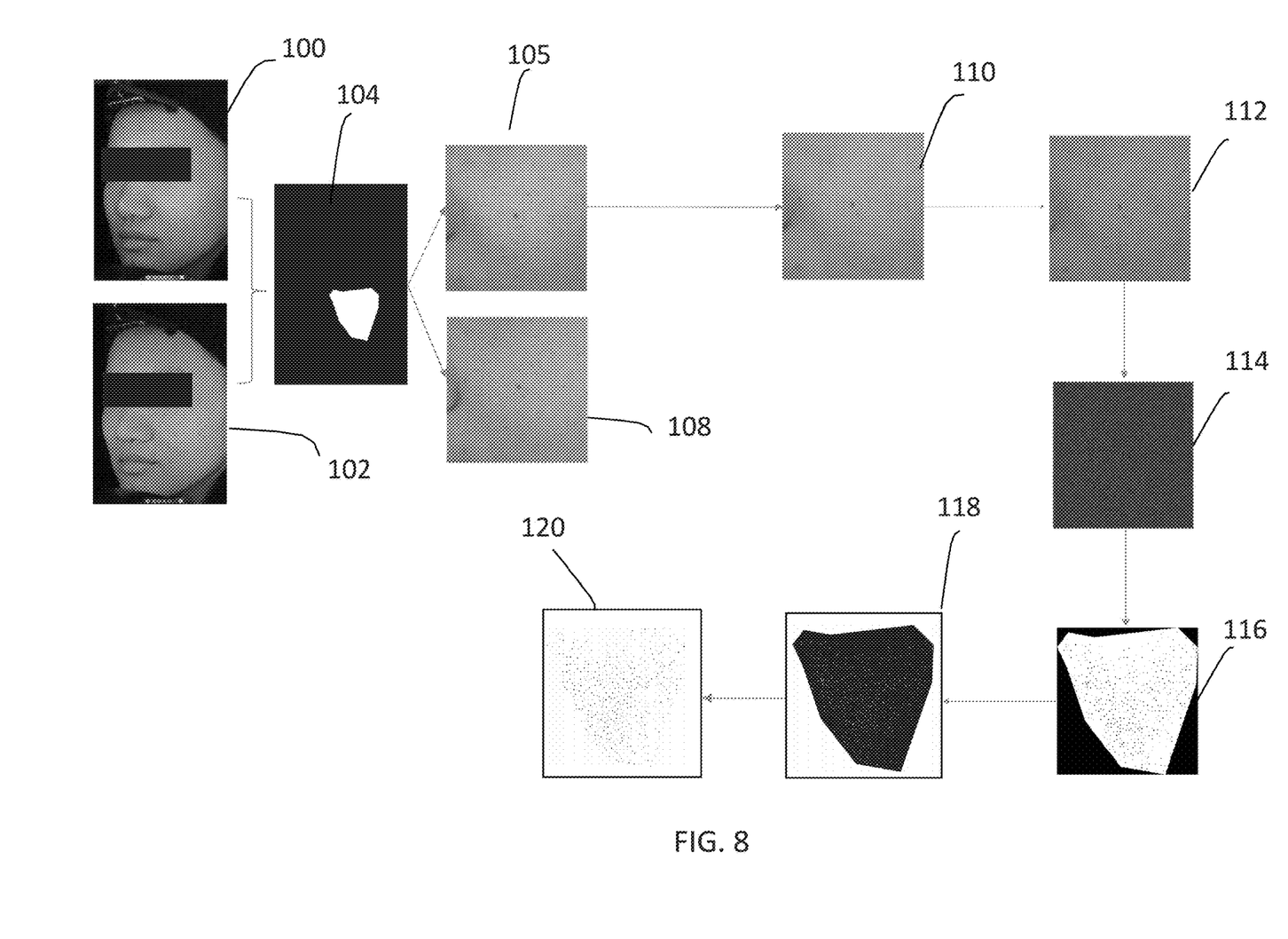
FIG. 8 depicts a flow diagram of a method for identifying a pore color of a plurality of skin pores, a method for determining a pore color contrast value of each of the skin pores, and a method for classifying the skin pores into one of a plurality of classifications in accordance with the present invention.

FIG. 8 depicts a flow diagram of a method for identifying a pore color of a plurality of skin pores, a method for determining a pore color contrast value of each of the skin pores, and a method for classifying the skin pores into one of a plurality of classifications, in accordance with the present invention. Each classification may be a predetermined class based on one or more of the following: pore color, pore color contrast value, pore geometry, and any combinations thereof.

A first image 100 and a second image 102 are captured by Visia®-CR imaging system (Canfield Scientific, New Jersey, USA), which is a commercialized clinical imaging device. The Visia®-CR imaging system comprises a Canon® 5D Mark II DSLR camera equipped with a full frame Complementary Metal-Oxide Semiconductor (CMOS) sensor. The first image 100 is a full-face or entire face Standard 2 (S2) image of a subject, and the second image 102 is a full-face or entire face cross polarized (XP) image of the subject. As full-face images are captured, a mask 104 is created to focus on the region of interest, which in these studies, is the cheek area. The first image 100 is cropped based on the mask 104 to obtain a cropped first image 105, and the second image 102 is cropped based on the mask 104 to obtain a cropped second image 108. The cropped first image 105, which is a RGB image comprising three channels (red, green, blue), is then converted into a YCbCr color space and luminance channel "Y" is selected to obtain a "Y" channel image 110.

Due to the geometry of the face and positioning of flashes that may come from the imaging system or any image capturing device, achieving uniform illumination across the face is very challenging. Uneven illumination is undesired when in feature detection from digital images. To improve illumination and/or enhance contrast of the "Y" channel image 110, histogram equalization, such as Contrast-Limited Adaptive Histogram Equalization (CLAHE), is performed on the "Y" channel image 110 to obtain a histogram-equalized image 112. The "Y" channel image 110 is divided into a set of tiles and illumination is improved and/or contrast is enhanced for each tile by performing CLAHE on each tile. Bilinear interpolation may be used to combine neighboring tiles.

Figure 9:
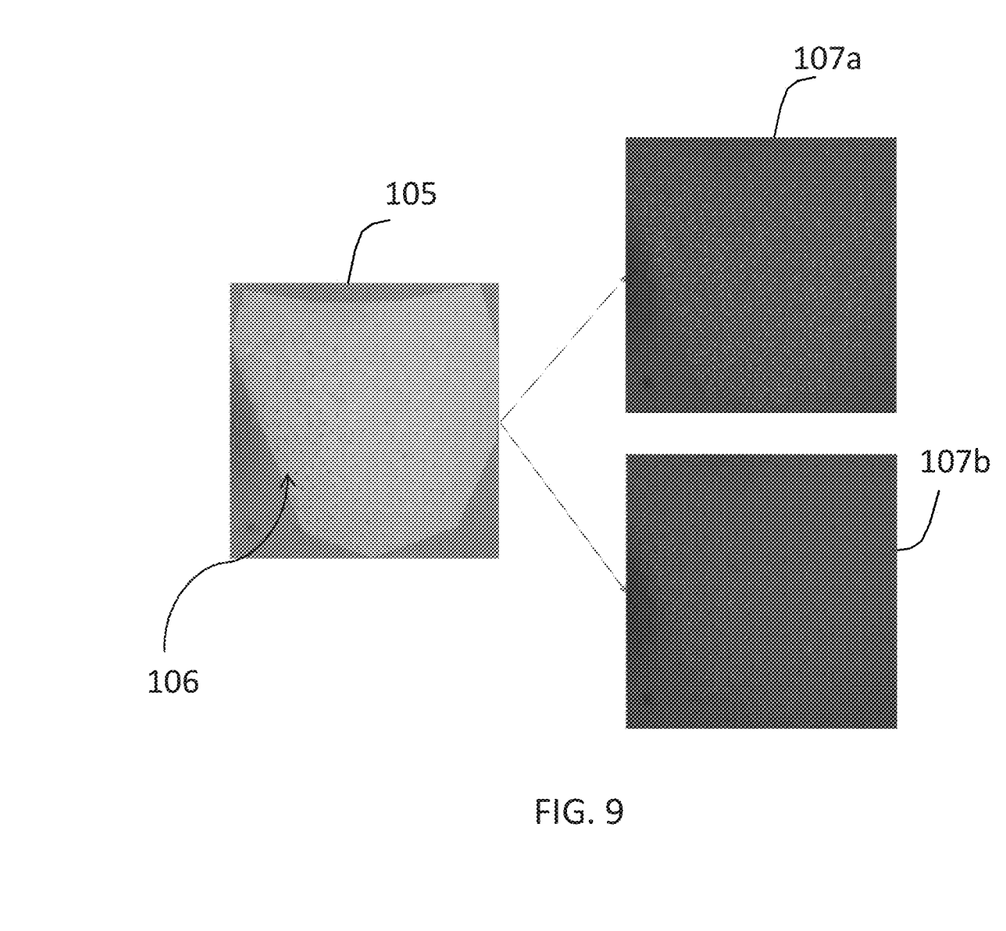
FIG. 9 depicts an image of a cheek area of a subject of FIG. 8 with a marked-out region of interest and the image after it has been processed with and without contrast-limited adaptive histogram equalization (CLAHE)

FIG. 9 shows the image 105 with a marked-out region of interest 106, and an image 107a without processing with CLAHE and an image 107b which is processed with CLAHE. The illumination and contrast of the image 107b is improved and the impact of uneven illumination due to geometry of the face and positioning of flashes and/or camera is reduced, which demonstrates the effectiveness of processing the image 105 with CLAHE.

As the studies relate to facial skin pore measurements, other skin feature or features (that is not a skin pore), which includes, but not limited to, one or more of the following: shine, line, spot, hair, mole, pimple acne, blackhead, whitehead, and any combinations thereof, may be considered as noise and may be removed from the histogram-equalized image 112. The histogram-equalized image 112 is filtered using a frequency filter, such as a Difference of Gaussian (DoG) filter, to remove such one or more skin features to obtain a filtered image 114.

The histogram-equalized image 112 is passed through the below DoG kernel where x is the distance from the origin in the horizontal axis, y is the distance from the origin in the vertical axis, and $\sigma_1$ and $\sigma_2$ are the standard deviation of two Gaussian distributions:

$$DoG = \frac{1}{2\pi\sigma_1^2} e^{\left[-\frac{x^2+y^2}{2\sigma_1^2}\right]} - \frac{1}{2\pi\sigma_2^2} e^{\left[-\frac{x^2+y^2}{2\sigma_1^2}\right]}$$

Image segmentation, such as adaptive thresholding, is performed on the filtered image 114, preferably together with binarization, to obtain a binary image 116. Optionally, a filter such as a watershed transformation filter, is applied to the binary image 116 for separating skin features which are connected, to obtain a filtered binary image 118. Optionally, a filter such as a size or shape filter, is applied to the filtered binary image 118 to obtain an extracted pore image 120. The extracted pore image 120 may be used to calculate pore geometry related statistics including, but not limited to, number, area, circumference, aspect ratio, orientation and cartesian coordinates of centroid.

Figure 10A:
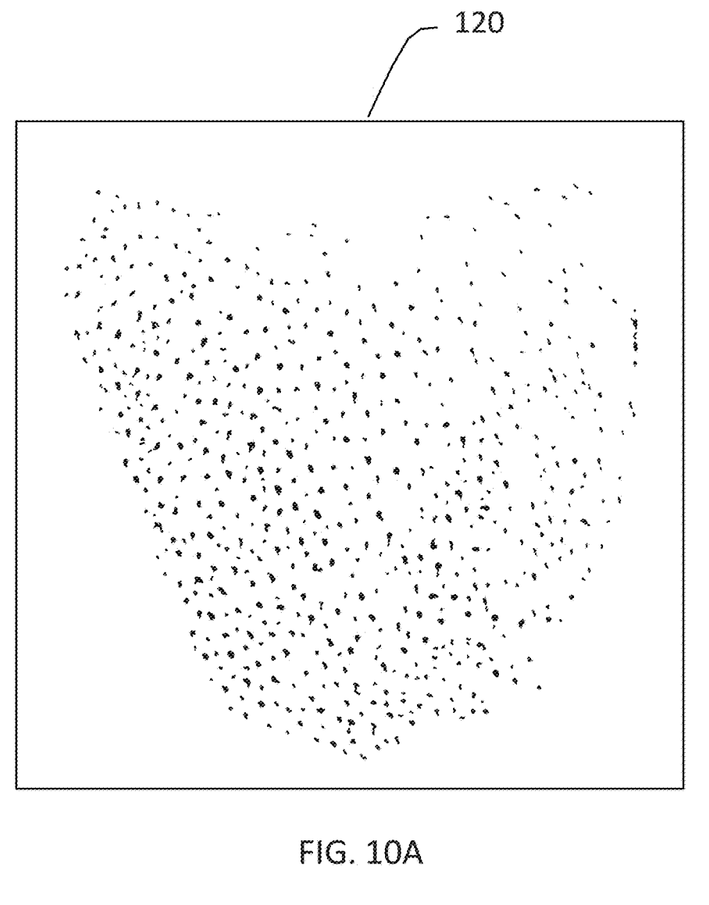
FIG. 10A depicts an extracted pore image from the flow diagram of FIG. 8.
Figure 10B:
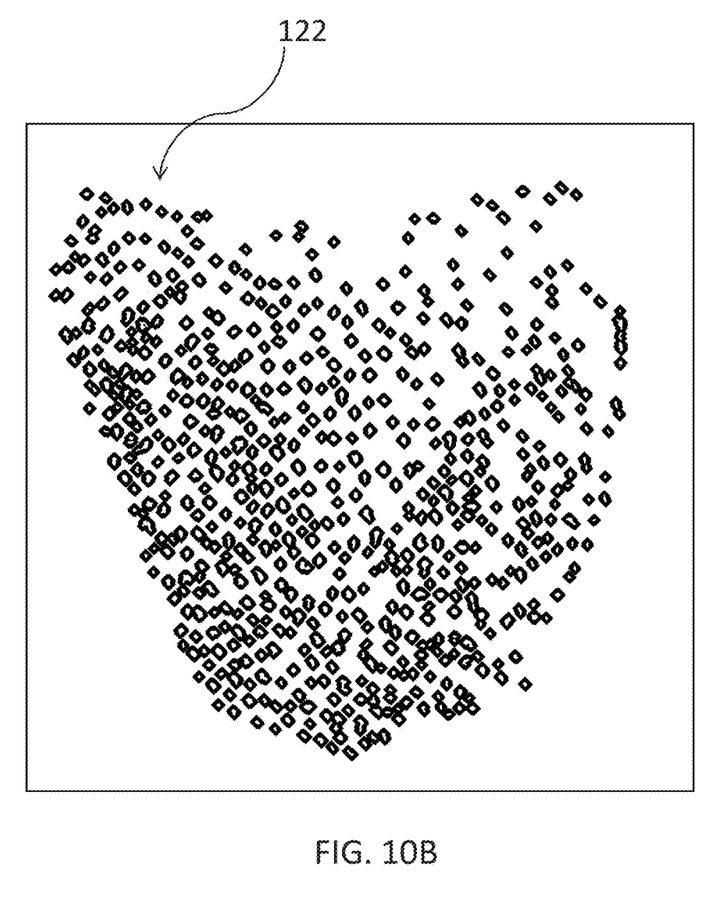
FIG. 10B depicts a defined adjacency area radially from the boundary of each of the pores of FIG. 10A.

The extracted pore image 120 may also be used to identify a boundary of each of the skin pores, and an adjacency area 122 that is radial from the identified boundary of each of the skin pores is defined, as shown in FIGS. 10A and 10B, respectively. The image 108 and the extracted pore image 120 is superimposed to identify a pore color within the identified boundary of each skin pore, and the image 108 and the defined adjacency area is superimposed to identify an adjacency area color. The identified pore color of each of the skin pores may be compared with the identified adjacency area of the respective skin pore to determine a pore color contrast value for each of the skin pores.

Although the S2 image 100 and the XP image 102 are taken within seconds one after the next, the subjects may have minor moments, for example, slight movements due to breathing. To minimize any effect due to minor moments, the XP image 102 may first be aligned with the S2 image 100 using a rigid intensity based image registration method to obtain a registered XP image. The registered XP image may be used to calculate colors. All colors are initially measured by RGB intensities which are then converted into CIE-LAB color space, which is the most established color space for skin measurements. Furthermore, pore color contrast value between the identified pore color of each of the skin pores and the identified adjacency area of the respective skin pore is calculated using CIE DE2000 formula.

An image analysis algorithm or method based on the present invention is developed using Matlab R2017a (MathWorks, Inc., Massachusetts, USA).

Pore Color Simulation Test

A subject who has darker pores in the infraorbital region is selected for a pore color simulation test. An image of the infraorbital region is captured by the Visia®-CR imaging system. Digital simulation is used to simulate various degrees of the color of the pores of the captured image. In this example, Adobe Photoshop CS6® is used to digitally simulate different degrees of pore lightening: (i) pore color is lightened by 10%; (ii) pore color is lightened by 25%; and (iii) pore color is lightened by 50%, relative to the original pore color.

TABLE 1

| Degree of Pore Lightening (%) | Pore Color Contrast Value | $R^2$ Value |
|---|---|---|
| 0% | 3.81 | 0.94 |
| 10% | 3.76 | |
| 25% | 3.36 | |
| 50% | 2.26 | |

Table 1 shows degree of pore lightening and the corresponding pore contrast value measured by the method of the present invention. It is believed, without being limited by theory, that when pore color is lightened, the pore color contrast value should decrease. A regression plot between pore contrast value and degree of pore lightening gives an $R^2$ of 0.94, which suggests that the relationship between two variables (i.e. pore lightening and pore color contrast value) is highly linear. A linear decrease of pore color contrast value against the degree of pore lightening proves the accuracy of the method of the present invention.

Figure 11A:
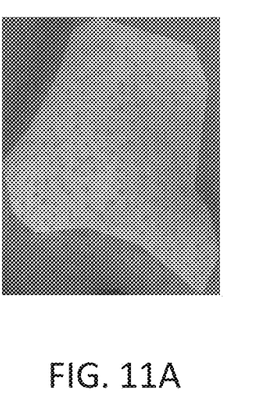
FIG. 11A depicts an image of a nasal area of a subject with a marked-out region of interest in accordance with the present invention.
Figure 11B:
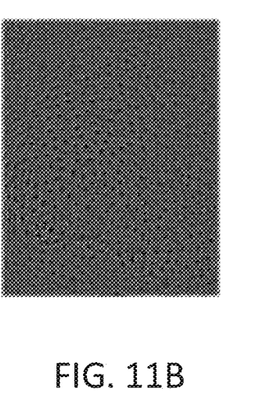
FIG. 11B depicts the image of the region of interest of FIG. 11A after it has been filtered with a Difference of Gaussian filter.
Figure 11C:
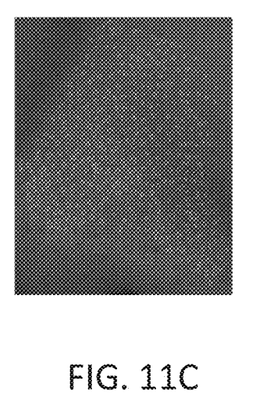
FIG. 11C depicts a superimposed image of the image of FIG. 11A and an extracted pore image of FIG. 11A.

The validation of the developed image analysis algorithm is done using the cheek region, in particular, the infraorbital region, since significant higher pore density is typically observed in such a region for majority of the subjects. It would be appreciated that other regions of interest, such as other facial areas or areas of the body, may be analyzed and processed as described above. For example, FIG. 11A shows enlarged pores in the nasal region of a subject which is marked-out as a region of interest, whilst FIG. 11B shows an enhanced image of the region of interest of FIG. 11A after a DoG filter is applied, and FIG. 11C shows the image after CLAHE is applied.

Advantageously, the present invention may be applied to regions of interest that are difficult to access, for example, uneven surfaces of the skin, areas of the skin with curvatures such as the nasal region, as compared to existing 3D imaging methods in which application of such methods is typically limited to regions which are easily accessible.

Figure 12A:
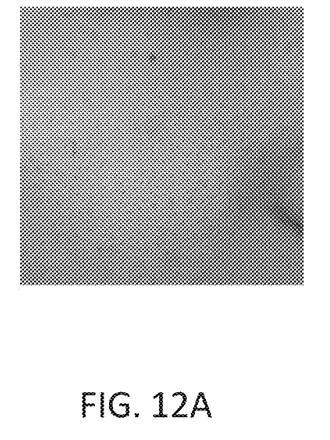
FIG. 12A depicts an image of a cheek area of a subject with dark pores in accordance with the present invention.
Figure 12B:
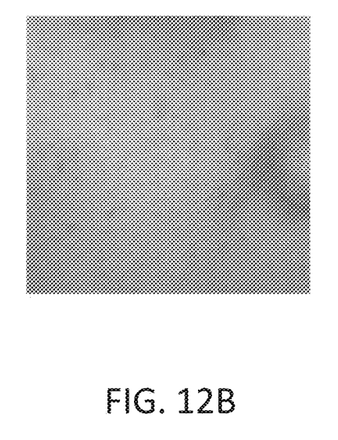
FIG. 12B depicts an image of a cheek area of a subject with light pores in accordance with the present invention.

Advantageously, the present invention may be applied to characterize different properties of skin pores, which may enable measurements of color of pores, color around pores and pore color contrast. FIG. 12A shows an image of a subject with 78% darker pores as compared to an image of a subject with lighter pores as shown in FIG. 12B, although the pores shown in FIG. 12A are only 25% larger in area. Pore severity may be differentiated based on color.

Advantageously, the present invention may be applied to analyze 2D images which makes it easy to implement in clinical trials. Furthermore, it is not limited to analyzing images captured by sophisticated imaging systems or devices; images captured from other sources such as consumer devices e.g. mobile cameras and the like, may also be used for analysis. Where it is not possible for images to be cross polarized when captured, it would be understood that suitable alternative image processing approaches may be implemented to such images for color measurements.

Other applications of pore and/or skin feature color, pore and/or skin feature color contrast value, and/or pore and/or skin feature intensity contrast value include, but are not limited to, simulation of aging or skin aging, predicting skin care product efficacy, application in beauty care or skin care devices or systems, such as applicators, diagnostics device or system, predictive models such as predicting perception of pore visibility of a subject, predictive models based on suitable training sets, simulation of age appearance, simulation of apparent skin age of a person, guiding a user to take a selfie, image processing for determining quality of a self-captured image, identifying and/or classifying hyperpigmented spots, simulation of skin aging and/or de-aging (e.g. US 2008/212894), simulation of wrinkle aging and/or de-aging (e.g. US 2009/028380), providing customized product recommendation (e.g. US 2017/0270593), determining spectral characteristics of an image (e.g. US 2017/0272741), generating graphical chromophore maps (e.g. US 2017/0270349, US 2017/0270691), assessing facial skin health (e.g. US 2017/0270350), and generating interactive image of facial skin (e.g. US 2017/0270348).

It will be understood that reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" All numeric ranges described herein are inclusive of narrower ranges; delineated upper and lower range limits are interchangeable to create further ranges not explicitly delineated. Embodiments described herein can comprise, consist essentially of, or consist of, the essential components as well as optional pieces described herein. As used in the description and the appended claims, the singular forms "a," "an," and "the" are intended to include the plural forms as well, unless the context clearly indicates otherwise.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for identifying a pore color of at least one skin pore, comprising:
   a. obtaining only one image of a subject, optionally cropping the obtained image to obtain a portion of the image; and performing a histogram equalization to the obtained image or the portion of the image to obtain a histogram-equalized image;
   b. filtering the histogram-equalized image to remove one or more skin features that are not a skin pore to obtain a filtered image; wherein the one or more skin features are chosen from shine, line, spot, hair, mole, pimple, acne, blackhead, and/or whitehead;
   c. segmenting a pore image from the filtered image, wherein the extracted pore image identifies a boundary of each of the skin pores; wherein the segmenting is performed by one or more of an adaptive thresholding method, color-based segmentation method, transform method, and texture method;
   d. superimposing the obtained image and the extracted pore image to identify the pore color within the identified boundary of each skin pore;
   e. defining an adjacency area radially from the identified boundary of each of the skin pores;
   f. superimposing the obtained image and the defined adjacency area to identify an adjacency area color of each of the skin pores; and
   g. comparing the identified pore color to the identified adjacency area color to determine a pore color contrast value of each of the skin pores.

2. The method of claim 1, wherein the defined adjacency area is in the range of 0.001 mm to 30 mm, from the identified boundary of each of the skin pores.

3. The method of claim 2, wherein the defined adjacency area is in the range of 0.005 mm to 1 mm, from the identified boundary of each of the skin pores.

4. The method of claim 1, wherein the step of filtering comprises using a frequency filter, wherein the frequency filter is chosen from a Fast Fourier Transformation filter, and/or a Difference of Gaussian filter.

5. The method of claim 1, wherein the segmenting is performed by the adaptive thresholding method.

6. The method of claim 1, further comprising classifying the at least one of the skin pores into a predetermined class based on one or more of a pore color, a pore color contrast value, a pore geometry, and combinations thereof.

7. The method of claim 1, wherein the image of the subject is a color image.

8. A method for determining a skin feature color contrast value of at least one skin feature, comprising:
   a. obtaining only one image of a subject, optionally cropping the obtained image to obtain a portion of the image; and performing a histogram equalization to the obtained image or the portion of the image to obtain a histogram-equalized image;
   b. filtering the histogram-equalized image to remove one or more skin features that are not a skin pore to obtain a filtered image; wherein the one or more skin features are chosen from shine, line, spot, hair, mole, pimple, acne, blackhead, and/or whitehead;
   c. segmenting a skin feature image from the filtered image, wherein the extracted skin feature image identifies a boundary of the at least one skin feature;
   wherein the segmenting is performed by one or more of an adaptive thresholding method, color-based segmentation method, transform method, and texture method;
   d. defining an adjacency area radially from the identified boundary of the at least one skin feature;
   e. superimposing the obtained image and the extracted skin feature image to identify a skin feature color within the identified boundary of the at least one skin feature;
   f. superimposing the obtained image and the defined adjacency area to identify an adjacency area color; and
   g. comparing the identified skin feature color to the identified adjacency area color to determine the skin feature color contrast value.

9. The method of claim 8, wherein the defined adjacency area is in the range of from 0.001 mm to 30 mm from the identified boundary of the at least one skin feature.

10. The method of claim 9, wherein the defined adjacency area is in the range of from 0.005 mm to 1 mm, from the identified boundary of the at least one skin feature.

11. A method for determining a skin feature intensity contrast value of at least one skin feature, comprising:

a. obtaining only one image of a subject, optionally cropping the obtained image to obtain a portion of the image; and performing a histogram equalization to the obtained image or the portion of the image to obtain a histogram-equalized image;
b. filtering the histogram-equalized image to remove one or more skin features that are not a skin pore to obtain a filtered image; wherein the one or more skin features are chosen from shine, line, spot, hair, mole, pimple, acne, blackhead, and/or whitehead;
c. segmenting a skin feature image from the filtered image, wherein the segmenting is performed by one or more of an adaptive thresholding method, color-based segmentation method, transform method, and texture method; wherein the extracted skin feature image identifies a boundary of the at least one skin feature;
d. defining an adjacency area radially from the identified boundary of the at least one skin feature;
e. superimposing the obtained image and the extracted skin feature image to identify an intensity within the identified boundary of the at least one skin feature;
f. superimposing the obtained image and the defined adjacency area to identify an intensity of the adjacency area; and
g. comparing the identified intensity within the identified boundary of the at least one skin feature to the identified intensity of the adjacency area to determine the skin feature intensity contrast value.

* * * * *